United States Patent [19]
Adomaitis et al.

[11] Patent Number: 4,675,730
[45] Date of Patent: Jun. 23, 1987

[54] VIDEO SURFACE INSPECTION SYSTEM

[75] Inventors: Paul R. Adomaitis, Level Green; Nicholaas L. Brouwer, Allegheny Township, Westmoreland County; Bernard J. Hobi, Upper Burrell Twp., Westmoreland County, all of Pa.

[73] Assignee: Aluminum Company of America, Pittsburgh, Pa.

[21] Appl. No.: 773,065

[22] Filed: Sep. 6, 1985

[51] Int. Cl.⁴ ............................................. H04N 7/18
[52] U.S. Cl. ..................................... 358/106; 340/675
[58] Field of Search ......................... 358/106, 93, 101; 340/675

[56] References Cited

U.S. PATENT DOCUMENTS

| | | | |
|---|---|---|---|
| 2,680,200 | 6/1954 | Hercock | 358/113 |
| 2,803,755 | 8/1957 | Milford | 358/106 |
| 3,049,588 | 8/1962 | Barnett | 358/106 |
| 3,081,379 | 3/1963 | Lemelson | 358/106 |
| 3,230,305 | 1/1966 | Kendrick | 358/106 |
| 3,379,829 | 4/1968 | Gambrell | 358/106 |
| 3,389,789 | 6/1968 | Watson | 358/106 |
| 3,868,478 | 2/1975 | Zeenkov | 358/93 |
| 4,063,282 | 12/1977 | Exton | 358/106 |
| 4,219,844 | 8/1980 | Ohsumi | 358/106 |
| 4,223,346 | 9/1980 | Neiheisel | 358/106 |
| 4,232,336 | 11/1980 | Henry | 358/106 |
| 4,240,110 | 12/1980 | Henry | 358/106 |
| 4,253,113 | 2/1981 | Decavel | 358/106 |
| 4,377,746 | 3/1983 | Kopineck | 356/430 |
| 4,403,294 | 9/1983 | Hamada | 358/106 |
| 4,449,818 | 5/1984 | Yamaguchi | 358/106 |
| 4,473,842 | 9/1984 | Suzuki | 358/106 |
| 4,539,561 | 9/1985 | Wulff | 340/675 |

Primary Examiner—Howard W. Britton
Attorney, Agent, or Firm—Elroy Strickland

[57] ABSTRACT

The invention comprises a system for continuously inspecting the surface of a moving object for defects therein while illuminating the surface of the moving object with both specular and/or diffused light of selected wavelengths, automatically detecting the presence of a defect, and automatically transmitting a visual image of a defect, when detected, to a storage vehicle capable of subsequent permanent display and electronic characterization of the visual image containing the defect.

3 Claims, 2 Drawing Figures

VIDEO SURFACE INSPECTION SYSTEM

BACKGROUND OF THE INVENTION

This invention relates to a system for inspecting the surface of a moving aluminum surface. More particularly, the invention relates to a system for automatically detecting flaws in the surface of a moving object and storing a visual image of the flaw for inspection thereof. Strobed illumination or electronic or mechanical shuttering are used to arrest surface motion to provide an undistorted view of surface characteristics.

DESCRIPTION OF THE PRIOR ART

The inspection of objects for defects using camera means has been used by Kendrick et al U.S. Pat. No. 3,230,305 for the automatic inspection and rejection of bobbins of yarn; by Henry U.S. Pat. Nos. 4,232,336 and 4,240,110 for detecting irregularities in crimped fiber; and by Exton U.S. Pat. No. 4,063,282 for monitoring the growth of fatigue cracks in a specimen subjected to a pulsating load.

Yamaguchi et al U.S. Pat. No. 4,449,818 uses different types of lighting to differentiate the types of irregularities on an object, using the brightness from oblique lighting to detect foreign substances on the surface of the object and perpendicular lighting to detect defects through shape recognition of a defect pattern. Recognition of irregular patterns is also shown in Hamada et al U.S. Pat. No. 4,403,294 wherein an image signal is quantized as a binary code and then compared with a predetermined reference pattern to determine whether the visual image contains a defect pattern.

Watson U.S. Pat. No. 3,389,789 shows a detector which is operated for marking or rejecting imperfect material when a video signal is of sufficient magnitude to exceed a threshold level of the detector and Gambrell et al U.S. Pat. No. 3,379,829 uses flaw detection means for selectively inspecting certain preselected portions of glassware for flaws while ignoring other portions.

Inspection means have also been used for moving objects, such as mail, by Zeenkov U.S. Pat. No. 3,868,478 who uses strobe lights to capture the image of an address on a letter by camera means for conveyance to television storage means and for display on a closed circuit television monitor.

Television monitoring cameras have also been used to monitor defects in moving sheets as shown in Decavel et al U.S. Pat. No. 4,253,113. In Kopineck et al U.S. Pat. No. 4,377,746, the optical image of such a moving sheet is stored for later viewing while Neiheisel et al U.S. Pat. No. 4,223,346 uses a charge coupled array and a lens between the camera which will magnify the length of the field, i.e., the direction of travel of a moving band, without magnifying the width. Ohsumi et al U.S. Pat. No. 4,219,844 detects the flaws in red hot slabs by adjusting the illumination to provide reflected light energy much larger than the radiation energy from the metal part.

However, while the prior art has provided a number of defect detecting devices, there remains a need for means which will inspect a moving aluminum surface, such as provided by casting, rolling, extruding, and operations otherwise related to the production of aluminum products. The need is for detecting defects based on comparing an image pattern obtained using particular illumination techniques with a reference image pattern. When a difference in the image patterns is detected, the image containing the difference is automatically transmitted for viewing or electronic processing.

SUMMARY OF THE INVENTION

It is, therefore, an object of this invention to provide an improved system for automatically detecting defects in a moving surface.

It is another object of this invention to provide an improved system for automatically detecting defects in a moving surface, and to transmit the image of a defect to an image storage device for evaluation.

It is yet another object of the invention to provide an improved system for automatically detecting defects by illuminating a reflective surface with specular or diffused light, or combinations thereof, and comparing the image with a known pattern and transmitting the image of the surface to a storage device for viewing only if the comparison indicates that a defect exists.

These and other objects of the invention will be apparent from the description and accompanying drawings.

In accordance with the invention, a system is provided for continuously inspecting the reflective surface of a moving aluminum object for defects therein, automatically detecting the presence of a defect, and transmitting an image of the defect to a device capable of storing the image containing the defect for subsequent permanent display and examination.

DESCRIPTION OF THE PREFERRED EMBODIMENT

Figure 1:
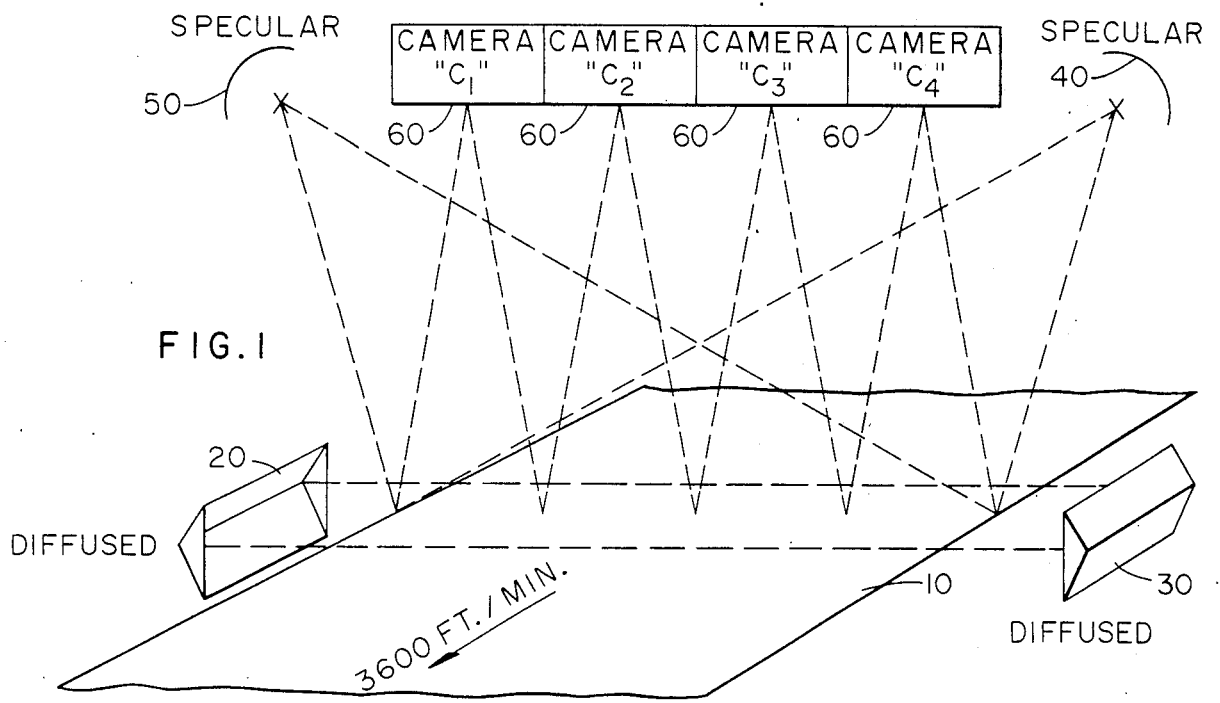
FIG. 1 is a schematic view of a portion of the detection system.

Referring now to FIG. 1, a portion of a traveling metal sheet 10 is shown illuminated by a series of light sources 20, 30, 40, and 50. Sources 20 and 30 provide diffused lighting of the surface of metal sheet 10 while light sources 40 and 50 provide specular illumination of metal sheet 10.

An image of selected areas of illuminated metal sheet 10 is then captured by one or more video cameras 60a through d which transmit corresponding electrical signals to respective video detectors 70a through d. When an image containing one or more defects is detected by one or more of the detectors 70, a triggering signal is automatically sent to a video storage unit 80; unit 80 is comprised of multiple storage devices, one for each of the detectors 70. That particular image is stored by 80 for subsequent electronic analysis or visual viewing via a freeze frame monitor 90. Monitor 90 allows a workman to visually detect and quantify any rejectionable defect that actually exists over the complete width of sheet 10 passing beneath cameras 60.

Electronic evaluation of the image for defect characterization is effected by a processing device 95. Such a device is interfaced at 97 with the freeze frame monitor and with a more permanent storage means 100. Hence, the image stored in video store 80 may also be conducted to a more permanent storage means 100, which may comprise a videotape, a computer, a laser disc or other suitable storage means.

Figure 2:
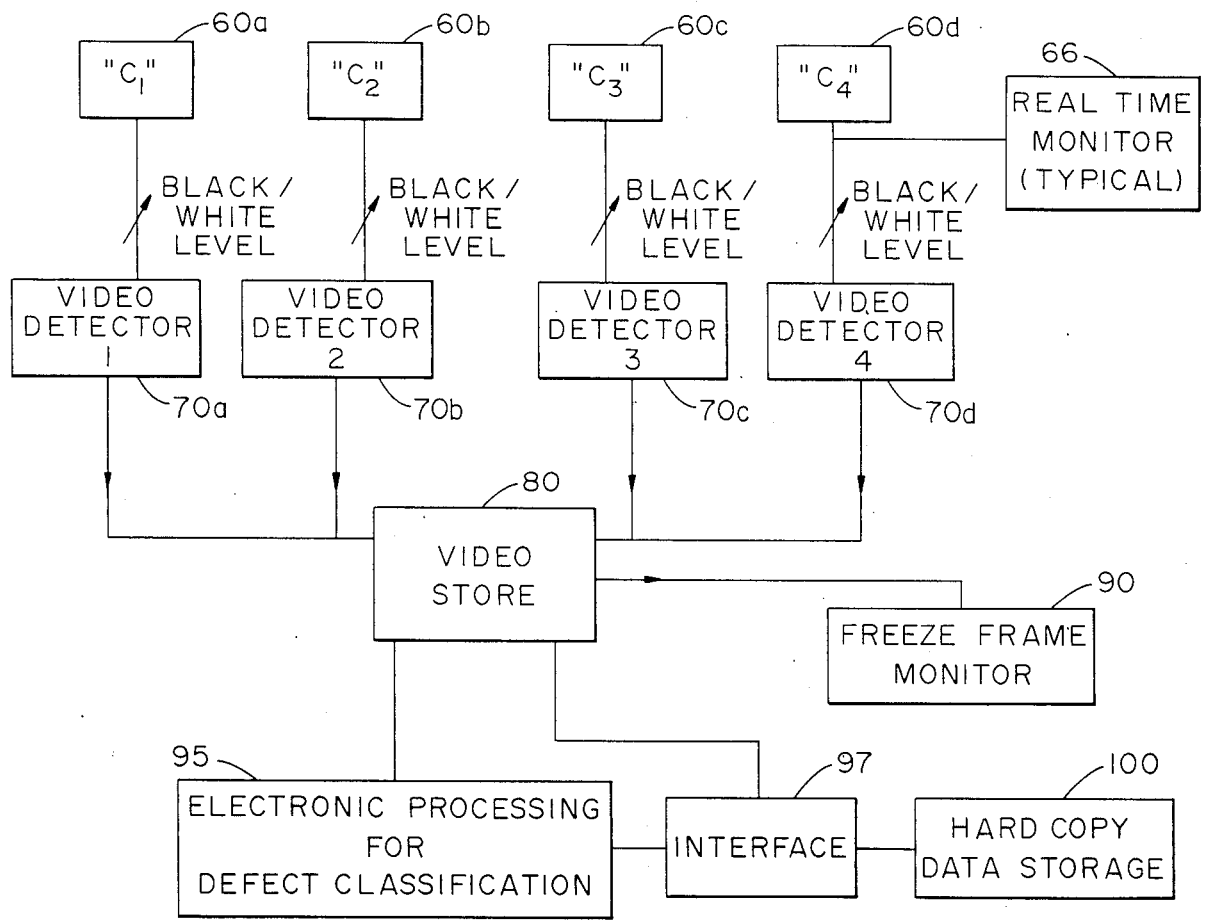
FIG. 2 is a block diagram of another portion of the detection system.

If desired, the image of the moving sheet may also be viewed in real time mode as well, such as from monitor 66 as shown in FIG. 2. However, it will be appreciated that the human eye may not be able to continuously perceive defects detectable by detectors 70 at maximum production web speeds.

In accordance with a preferred embodiment of the invention, moving metal sheet 10 is illuminated by diffused and/or specular illumination to provide a more homogeneous coverage of the web surface. A combination of diffuse and specular illumination can be used to highlight variations in the surface being examined. Also, in a particularly preferred embodiment, the surface is illuminated by light in the long-wave invisible (red) portion of the spectrum to more fully match the sensitive spectrum of the image sensors used in video cameras and enhance the reflecting characteristics of the surface.

Being invisible, personnel are not hampered by high-intensity strobed illumination processes. The reflected or scattered energy from illumination sources 20, 30, 40, and 50 may be constant or may be strobed depending upon whether shuttered camera means are employed. Commercially available strobe lights or camera shutters can capture images of the moving surface at a rate of sixty or multiples of sixty per second. This typically will permit 100% down web inspection of a sheet surface traveling at 1800 feet per minute (or multiples thereof) if the field of view (in the direction of travel) of the camera 60 represents one foot. In such case the image resolution represents 512 scan lines on the television screen, which is the NTSC television broadcast standard. In order to obtain a blur-free image of a moving surface, either the illumination source or the camera sensor must be strobed. This can be accomplished by either a pulsed illumination source or by a mechanically shuttered camera sensor. In both cases the illumination source utilized needs to be of high intensity.

As shown in FIG. 2, the energy reflected from illuminated metal sheet 10 is captured by one or more video camera means 60 for conversion into an electrical signal which is transmitted to respective detectors 70. Video cameras suitable for the practice of the invention are readily available from commercial sources such as RCA, GE, Panasonic, Sony, and Phillips. Video detectors which may be used in the practice of the invention also comprise commercially available equipment such as a model 630 video detector, available from Colorado Video, Incorporated located in Boulder, Colo.

From a standpoint of the width of the moving metal sheet, more than one camera can be used to cover the moving sheet area. As shown in FIG. 1, four video camera means are mounted side by side to insure simultaneous inspection of the entire width of, for example, a 48-inch width metal sheet; this entire width is captured by 80 for display at 90. The number of cameras 60 required is dependent upon the detail of the surface variation to be detected. Optical magnification can provide the detail sought but reduces the field of view of the camera. As a consequence, more than one camera may be required if the field of view of the camera is less than the area of the surface of interest.

The reflected image, which is captured by video camera means 60, comprises varying intensities known in the art as gray scale levels. The particular gray scale levels, representing a metal surface free of defects, are empirically determined to calibrate the equipment using samples, respectively either free of defects, or containing certain types of known defects. Some defects will absorb or scatter more light than a defect-free surface while other defects will absorb or scatter less light than a defect-free surface. Hence, the equipment is standardized to provide both a minimum and a maximum gray scale level which represents the range of intensities that will be reflected from a surface free of defects.

When an electronic signal, such as from a surface defect, results in a gray scale level outside the standardized range, detector 70 senses this signal and activates the corresponding video unit 80 which will store for display of the image on monitor 90. Basic equipment to accomplish this is state-of-the-art. Thus the detection, storage, and display of images containing defects is automatic, requiring no visual and manual manipulation.

The stored image frame is displayed on monitor 90 to permit visual examination and study of the image purporting to contain a defect to determine whether or not a rejectionable defect actually exists. The image remains on monitor 90 until the occurrence of another defect or at the option of operating personnel.

As previously discussed, the image of the defect may also be transmitted to more permanent storage mediums such as videotape or disc (100) for visual or electronic evaluation and characterization by computer means.

Thus the invention provides a system for automatic monitoring of moving surfaces such as a moving metal sheet to detect defects on the surface and to transmit to a storage device an image of the particular portion of the surface containing a defect for visual and electronic characterization. In this way a large quantity of material may be rapidly surveyed with automatic equipment while an operator may more meticulously view images of only those portions of the moving object which the automatic equipment has singled out as possibly containing defects. Furthermore, by using specular and/or diffused illumination of selected wavelength, the sensitivity of the equipment to various types of defects is materially enhanced.

While the invention has been described in terms of preferred embodiments, the claims appended hereto are intended to encompass all embodiments which fall within the spirit of the invention.

What is claimed is:

1. A method of continuously and automatically monitoring broad surfaces of a rapidly moving metal material for the detection and analysis of surface variations which exceed established acceptable surface conditions for the purpose of determining the occurrence of surface defects that are considered rejectionable and for providing accurate defect classification of the same, comprising:

homogeneously exposing the moving surface to visible and/or invisible specular and diffused electromagnetic radiation in a selected range of wavelengths to enhance surface features and thereby aid detection of surface defects, rendering the rapidly moving surface momentarily motionless, detecting the presence of one or more rejectionable defects with a plurality of sensors located to view the entire width of the material, transmitting an electronic image of the area containing a defect from one or more of the sensors to a device for storing the image for subsequent display and analysis, the image containing grey scale levels that represent varying intensities of electromagnetic energy reflected by the defect, providing a range of grey scale levels that represent the range of intensities of electromagnetic energy reflected from a surface that is free of rejectionable defects, comparing the grey scale levels of the image with the defect with the range of grey scale levels that represent a surface free of rejectionable defects, and viewing and analyzing only those images of the surfaces on a freeze frame monitor that have grey scale levels outside the grey scale range of intensities that indicate a surface free from rejectionable defects.

2. The method of claim 1 including the steps of:

directing the specular light from a position above the moving surface while the diffused radiation is directed in a direction substantially parallel to the surface, with both types of radiation being positioned to homogeneously cover the entire width of the surface.

3. A method of continuously and automatically monitoring broad surfaces of rapidly moving metal material for the detection and analysis of surface variations which exceed established acceptable surface conditions for the purpose of determining the occurrence of surface defects that are considered rejectionable and for providing accurate defect definition and classification of the same, comprising:

homogeneously exposing the moving surface to invisible and/or visible specular and diffused electromagnetic radiation in a selected range of wavelengths to enhance surface features and thereby aid detection, rendering the moving surface momentarily motionless, capturing images of one or more rejectionable defects on the moving surface across the width thereof at a rate of sixty per second, or multiples thereof, for a distance of one foot of the surface in the direction of travel at a speed of 1800 feet per minute, or multiples thereof, using side-by-side video cameras employing the NTSC standard of 512 scan lines per frame, transmitting an electronic image of the area containing a defect from one or more of the cameras to a device for storing the image for subsequent display and analysis, the image containing grey scale levels representing the intensities of energy reflected by the defect, providing a range of grey scale levels that represents the range of intensities of electromagnetic energy reflected from a surface that is free of rejectionable defects, comparing the grey scale levels of the image with the defect with the range of grey scale levels that represent a surface free of rejectionable defects, and viewing and analyzing only those images of the surfaces on a freeze frame monitor that have grey scale levels outside the grey scale range of intensities that indicate a surface free from rejectionable defects.

* * * * *